United States Patent [19]

Stevens

[11] Patent Number: 5,575,767
[45] Date of Patent: Nov. 19, 1996

[54] METHOD AND APPARATUS FOR HIGH PRESSURE ONE-WAY FLUID VALVING IN ANGIOGRAPHY

[76] Inventor: Robert C. Stevens, 18265 NW. Highway 335, Williston, Fla. 32696

[21] Appl. No.: 307,347

[22] Filed: Sep. 16, 1994

[51] Int. Cl.$^6$ .................................................. A61M 31/00
[52] U.S. Cl. ........................... 604/53; 604/247; 137/539; 251/149.6
[58] Field of Search ................................. 604/30, 31, 33, 604/80, 81, 246, 247, 249, 284, 49, 52, 53; 137/533, 614.2, 535, 539; 251/149.6, 149.7

[56] References Cited

U.S. PATENT DOCUMENTS

| | | | |
|---|---|---|---|
| 3,503,385 | 3/1970 | Stevens . | |
| 3,570,484 | 3/1971 | Steer | 604/249 |
| 4,681,559 | 7/1987 | Hooven | 604/9 |
| 5,041,087 | 8/1991 | Loo et al. | 604/83 |
| 5,401,255 | 3/1995 | Sutherland et al. | 604/247 |

*Primary Examiner*—Corrine M. McDermott
*Attorney, Agent, or Firm*—Fay, Sharpe, Beall, Fagan, Minnich & McKee

[57] ABSTRACT

A method and apparatus is provided for high pressure one-way fluid valving in angiography. The method includes inhibiting the flow of a sterile saline solution through a catheter lumen using the pressure of an opaque dye injected therethrough. A one-way fluid valve connects a pressurized source of saline solution to an inlet fitting of a catheter Y adapter. A second inlet fitting of the Y adapter is connected to a high pressure opaque media source through a gate valve. The one-way fluid valve is sensitive to a pressure differential thereacross to selectively open and close in response to the pressure within the catheter lumen versus the pressure of the saline solution. The one-way fluid valve includes a stainless steel check ball, a stainless steel biasing spring and double sealing O-ring adapted for radial compression by the stainless steel biasing spring and the pressure differential across the valve. The biasing spring has a spring constant commensurate with the saline solution pressure in order to open substantially immediately after the opaque media injection terminates. A female end of the valve includes a 360° luer fitting or hub for structural integrity and the male end of the valve includes a threaded cap member adapted to receive and engage a female 360° luer fitting. Unthreading the cap member from the valve separates the female 360° luer fitting from the tapered male surface of the valve.

6 Claims, 4 Drawing Sheets

5,575,767

METHOD AND APPARATUS FOR HIGH PRESSURE ONE-WAY FLUID VALVING IN ANGIOGRAPHY

BACKGROUND OF THE INVENTION

The subject invention is directed to the art of vascular catheters and, in particular, to methods and apparatus for the maintenance of clot-free catheter lumens in surgical procedures such as angiography.

As a general principal, in the field of angiography there is a constant need to maintain the lumen of a catheter continually filled or washed with a sterile solution such as a saline solution, or with an opaque media. This is done in order to reduce the possibility of blood entering the lumen and forming a clot therein. These clots are not easily seen forming and often impossible to detect. In the event that a clot does form, it could be inadvertently injected into the vascular system with disastrous results.

In performing the procedure of catheterization, there are a number of diverse functions which must be carried out by the surgeon using a catheter. These functions include monitoring the pressures within the vessels, injecting opaque media at a target site and providing a means to constantly flush or maintain the catheter at all times filled with saline solution to prevent clots when other media is not being injected through the catheter lumen.

To add to the above difficulties, many procedures require large amounts of opaque media to be rapidly injected into the target site. Frequently, to achieve this rapid injection, pressure at the proximal or hub end of the catheter often reaches 1,000 PSI. One explanation for the necessity of such high pressures and large volumes of opaque media flowed over a short period of time is that the vessels of an organ such as a kidney must be filled very quickly in order to obtain an X-ray image before the heart pumps the opaque dye media from the target site and into the body's vascular system. For certain procedures, one or two heartbeats are all that is necessary for the dye to be of little or no use at the target site for imaging purposes.

Angiographic catheters such as described in my earlier U.S. Pat. No. 3,503,385 and my co-pending U.S. application Ser. No. 08/144,202 filed Oct. 27, 1993, the teachings of which are incorporated herein by reference, have been ruggedized or otherwise designed to withstand the high pressures mentioned above. However, heretofore, it has been difficult or nearly impossible with existing equipment to ensure that sterile saline solution continuously flows through the catheter lumen substantially immediately after the dye injection in order to keep the lumen flushed at all times to prevent clots.

One prior art method and apparatus used to control the saline fluid has involved a stopcock which is manually operated as fast as possible in order to quickly gate the saline flow on and off. However, given that there are often a plurality of stopcocks mounted on a single manifold to control other catheterization functions such as connections to pressure monitoring equipment or the like, surgeons find it difficult to first locate and then operate the correct stopcock in typically hurried moments of a catheterization procedure. Further, in the urgency or quick pace of a catheterization, it is possible to overlook whether all of the stopcocks mounted to a manifold are properly opened or closed. In some catheterization functions such as pressure monitoring, a stopcock which inadvertently remains closed becomes immediately obvious. This is not so with the saline line used in catheterization. It could be disastrous if the saline line is permitted to remain closed after the dye is injected for the reasons stated above.

Therefore, it is desirable to provide a simple and reliable method and apparatus to ensure that the saline line supplying a catheter assembly is operated automatically. This method and apparatus should preferably provide a solution which reduces the number of personnel responsibilities and patient risks associated with catheterization procedures such as angiography.

BRIEF SUMMARY OF THE INVENTION

The subject invention provides a simple and effective method and apparatus for high pressure one-way fluid valving in angiography. In the present invention, all bodily fluids including blood are prevented from entering the distal lumen opening of a catheter during surgical procedures by a constant wash of a one of a saline solution or an opaque media.

Generally, the subject invention includes a specialized saline fluid check valve for use in combination with a catheter assembly including an elongate hollow catheter and a source of a pressurized saline solution. The check valve is sensitive to a pressure differential between the pressure within the catheter lumen and the pressure of the saline solution. Further, the check valve is designed to withstand a reverse pressure in excess of that typically experienced when an opaque media is injected into a target site which, as identified above, is typically 1,000 PSI. In an absence of a pressure differential, the check valve is biased closed.

In accordance with a further aspect of the invention, there is provided a valve for use in combination with an elongate hollow catheter and a source of a first pressurized fluid. The valve includes a substantially tubular body having movable means therein for opening a fluid passage through the body when in a first position and closing the passage when in a second position. Biasing means are carried within the tubular body for biasing the movable means in the second position. Preferably, the movable means is a stainless steel check ball and the biasing means is a stainless steel spring. Also, in order to ensure a proper complete seal, it is preferable that the substantially tubular body include a rubber O-ring sealing member for sealing between the stainless steel check ball and a corresponding shoulder region of the substantially tubular body.

In accordance with a more limited aspect of the invention, the substantially tubular body is adapted on a first end for connection to a source of saline solution using a full contact or 360° type female luer fitting for maximum strength. The body is adapted on a second end for connection to a catheter device or to a "Y" adapter which is in turn attached to a catheter. The second end includes a male luer taper and a threaded cap member to securely mate the fitting to the saline line which leads to the catheter device. The cap member prevents separation of the fitting from the saline line when tightened and actively assists in separating the fitting from the saline line when manipulated in a loosening direction.

In accordance with yet still a further aspect of the invention, there is provided a catheterization method including communicating a first fluid from a source of the first fluid to the lumen of a catheter through a first fluid supply channel at a first pressure; and, communicating a second fluid from a source of the second fluid to the lumen of the catheter through a second fluid supply channel at a second pressure while simultaneously inhibiting communicating the first fluid flow using the second pressure. Preferably, the first and second fluids are a sterile saline solution and an opaque dye media respectively. Further, the second pressure is greater than the first pressure.

According to still yet a further aspect of the invention, the catheterization method includes the step of reapplying the saline solution fluid flow substantially immediately after the flow of the opaque media is terminated.

A primary advantage of the invention is that the flow of saline solution is automatically stopped during the dye injection of the opaque media and substantially reapplied after the opaque media flow has stopped.

Still another advantage of the invention is catheterization procedures, in particular angiographic procedures, are made simple by reducing the risks and responsibilities involved therewith.

Still other advantages and benefits of the invention will become apparent to those skilled in the art upon a reading and understanding of the followed detailed description.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein.

DETAILED DESCRIPTION OF THE PREFERRED EMBODIMENTS

Figure 1:
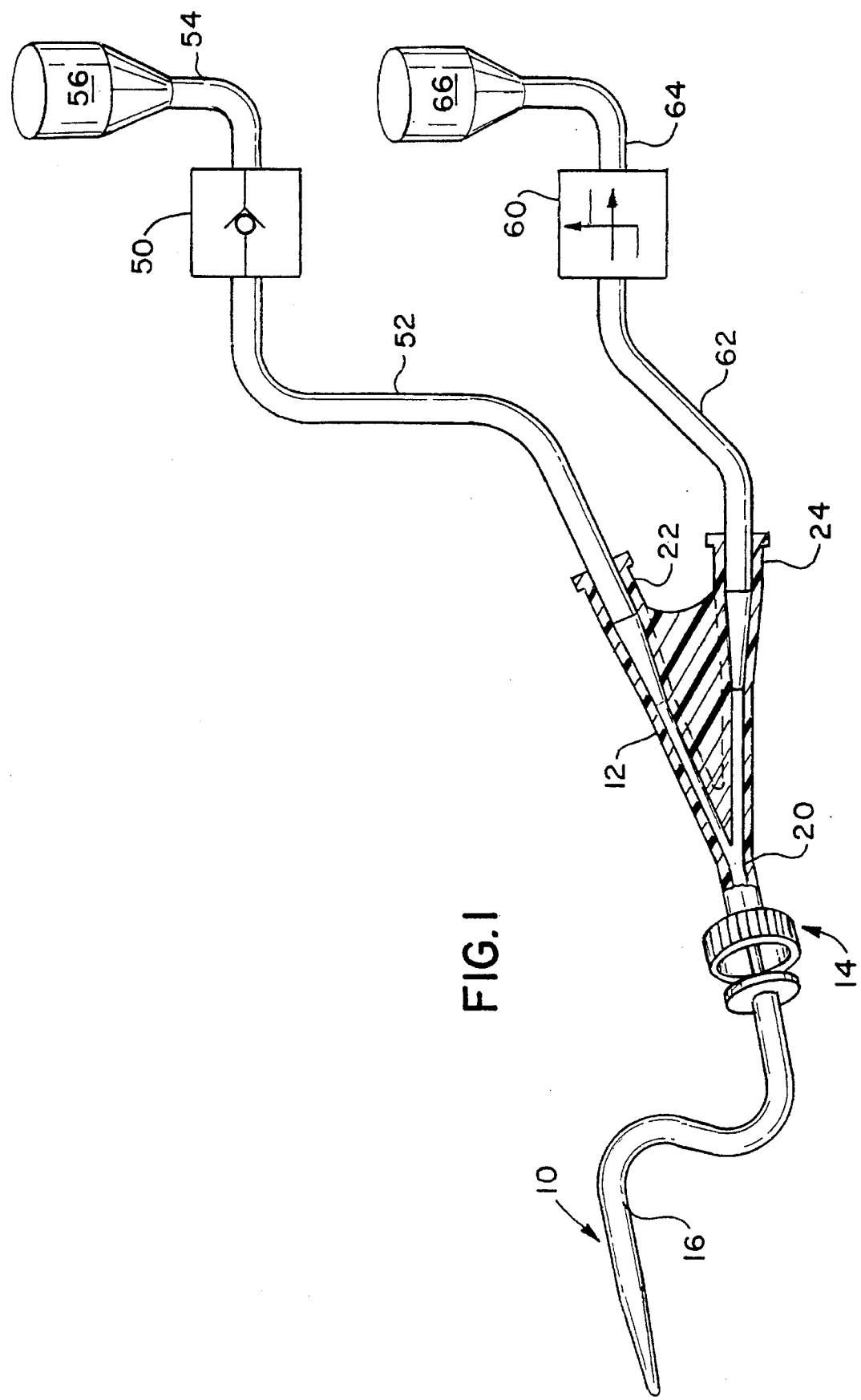
FIG. 1 is a cross-sectional view of a typical catheter "Y" connector in combination with a one-way fluid check valve according to the present invention.

As shown in FIG. 1, a catheter 10 is adapted for fastening to the forward end of a "Y" connector 12 by a conventional male Luer Lok arrangement 14. The catheter 10 consists of a tubular body portion 16 which is typically about 40 inches long and is preferably made of flexible plastic material.

The "Y" connector includes a forward fluid supply channel portion 20 which connects to a first and second inlet fittings 22, 24 respectively. The first inlet fitting 22 is connected to the one-way fluid valve 50, illustrated schematically in FIG. 1, through a first saline solution conduit 52. A second conduit 54 connects the one-way fluid valve 50 to a pressurized source of the saline solution 56.

The second inlet fitting 24 is connected to a suitable gate valve 60 through a first high pressure conduit 62. The gate valve 60 is in fluid communication with a high pressure source 66 of an opaque media through a second high pressure conduit 64.

The gate valve operates at a simple on/off fluid mechanism. In the preferred embodiment illustrated, the pressurized source of saline solution 56 is maintained at about 300 mm. of mercury pressure. On the otherhand, as described above, the pressurized source of opaque dye media 66 is maintained at about 1,000 PSI.

Figure 2:
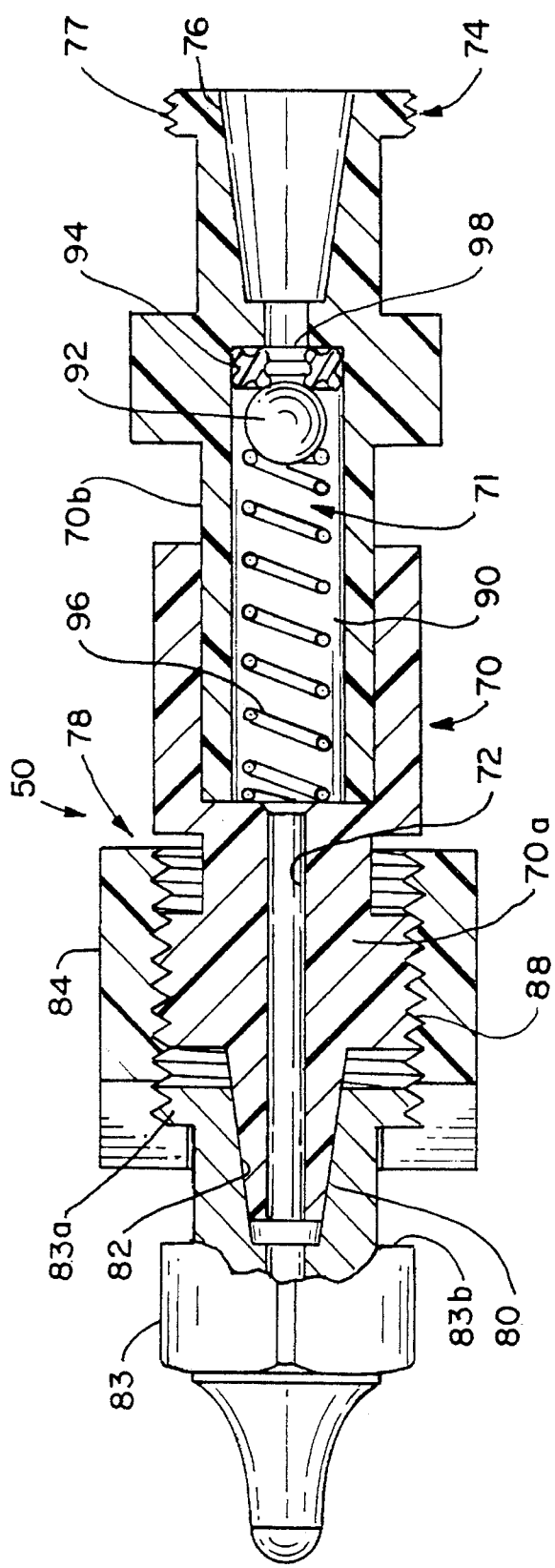
FIG. 2 is a cross-sectional view of the one-way fluid valve according to the present invention.

With reference next to FIG. 2, the preferred embodiment for the one-way fluid valve 50 will be described in greater detail. As seen therein, a main valve body 70 is an elongate hollow tubular member defining a valve chamber 71 and a fluid passageway 72 therethrough. Body 70 is formed of two components 70a and 70b telescopically joined and suitably bonded to form an effectively unitary structure. The proximal end 74 of the main body portion 70b is adapted for connection to the pressurized source of the saline solution 56 by means of a female Luer hub fitting 76. In the preferred embodiment, the female Luer hub fitting 76 is of the 360° contact type.

The female fitting 76 includes a continuous circumferential ridge or raised portion 77 which is suitably externally threaded for selective engagement with a corresponding male luer fitting. The full 360° engagement of the raised portion 77 with the male luer fitting ensures maximum structural integrity preventing a "blow off" of the valve 50 from the fluid conduit when subjected to high pressure bursts. When the valve 50 is formed of a plastic material such as in the preferred embodiment, the added strength provided by the continuous circumferential raised portion 77 is particularly desirable.

The distal end 78 of the main body portion 70a, is adapted to receive the first conduit 52 by means of a male Luer taper 80. The male standard Luer taper 80 engages a corresponding female Luer taper fitting 82 connected to the conduit 52 through means of an appropriate Luer fitting 83 and in combination with a threaded cap member 84. The Luer fitting 83 has a 360° locking ring 83a on the hub to cooperate with cap 84 to resist the high pressures it must experience. The cap member locks the male luer fitting to the female luer fitting to prevent their separation or "blow off" during bursts of high pressure.

Figure 2A:
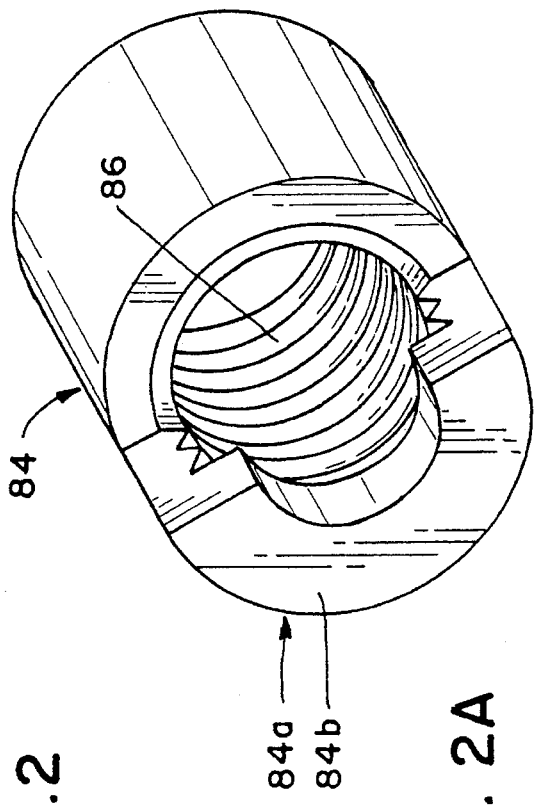
FIG. 2a is a perspective view of an end cap used in the valve of FIG. 2.

The threaded cap member 84 is best seen in FIG. 2a and is provided with internal threads 86 that engage corresponding external threads 88 formed on the main body portion 70a. End 84a of cap 84 is cut away in a semi-cylindrical pattern as shown to allow installation of the locking ring 83a into the cap member and removal of fitting 83 when the cap 84 is threaded outwardly to the left on body portion 70a. It should be noted that fitting 83 has a face 83b that is engaged by end face 84b of cap 84 during the unthreading step to force the fitting 83 off hub 80. The mechanical advantage or multiplexer provided by the threaded engagement with the valve body assists in separating the tapered fitting surfaces for ease of manipulation during surgical procedures.

To provide the one-way fluid valving described above, the main body portion 70b includes the central hollow region 90 that forms valve chamber 71 within which is disposed a stainless steel check ball 92 biased against a valve seat defining seal ring 94 by means of a stainless steel spring 96. The seal ring 94 is preferably of the double seal type, such as a unique commercial type known as a "Quattro Seal". The double seal of the O-ring helps to overcome sealing deficiencies which are caused by the crystalline structure of some of the opaque medias used in many catheterization and angiographic procedures. The "double seal" results from a pair of circular raised ribs on each side of the O-ring. A first of the rib pairs engages a surface of the valve body and a second of the pair engages the check ball surface. The main body portion 70 defines a shoulder region 98 which is substantially planar and adapted for fluid tight engagement with the O-ring 94. The spring constant of the stainless steel spring 96 is selection to be such that the ball 92 opens in response to the pressure of the saline solution and in an absence of the opaque media pressure such as when the gate valve 60 is closed.

Figure 3:
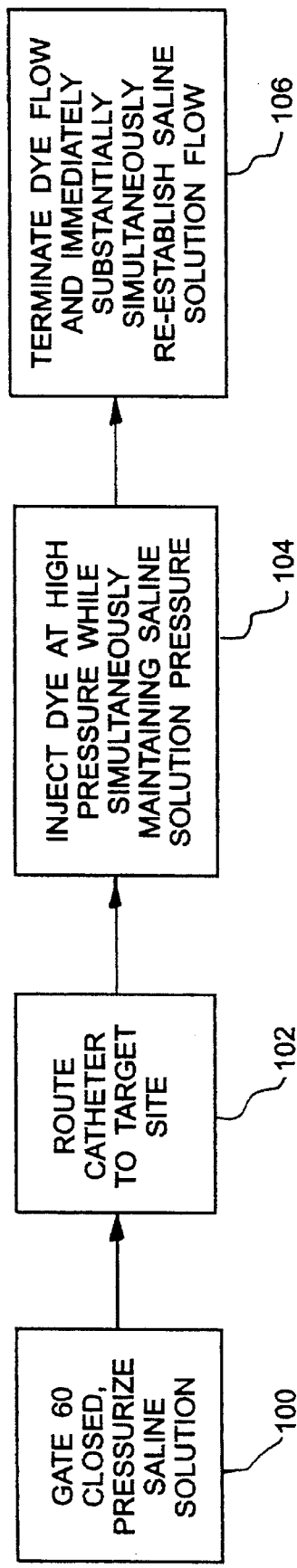
FIG. 3 is a flow chart illustrating a preferred method according to the present invention; and, FIG. 4 is a fluid flow timing diagram corresponding to the flow chart of FIG. 3.
Figure 4:
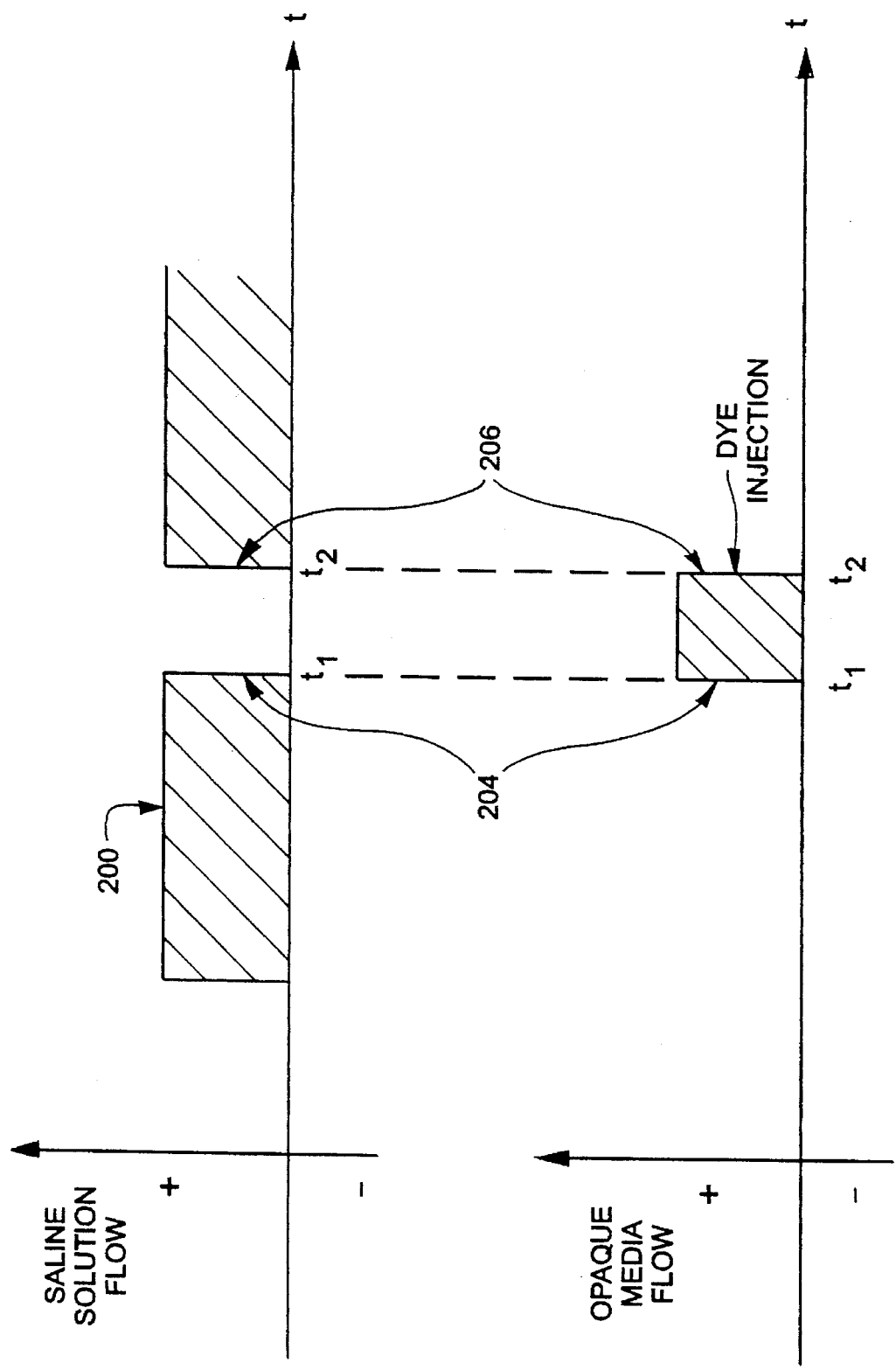

Turning to FIGS. 3 and 4, a preferred method of operating the one-way fluid valve in combination with a catheter assembly will be described. Initially, the gate 60 is closed and the saline solution source 56 is pressurized at step 100. As can be seen with reference to FIG. 1, in this mode of operation, the catheter apparatus administers a saline flush (200 FIG. 4) originating from the pressurized saline solution source 56, through the one-way fluid valve 50, through the first inlet fitting 22 and outward into the catheter 10 through the forward fluid supply channel portion 20. Next, while the saline solution is permitted to flow out of the distal end of the catheter, the catheter is manipulated to route the catheter tip to the target site 102. Once at the site, the surgeon prepares to administer the appropriate quantity of opaque media solution at an appropriate pressure.

At step 104, the surgeon operates the gate 60 causing the dye to be injected at high pressure. The opaque media flows (204 FIG. 4) through the gate 60, the high pressure conduit 62, the second inlet fitting 24 and out of the "Y" adapter 12 into the catheter 10. Under this condition, the pressure differential across the one-way fluid valve 50 is such that the stainless steel ball is urged to a closed position radially compressing the 0-ring 94. Although the saline solution is maintained at the 300 mm. of mercury pressure, the pressure differential across the one-way fluid valve is substantial given that the opaque media is typically established at 1,000 psi. The saline solution flow stops (204 FIG. 4).

Lastly, at step 106 the opaque media injection is terminated whereupon the saline solution flow is immediately and substantially simultaneously re-established (206 FIG. 4). Note from FIG. 4 that at all times the pressure within the catheter lumen is positive "+" indicating a positive internal lumen pressure to preclude blood flow therein thus preventing clotting.

The invention has been described with reference to the preferred embodiments. Obviously, modifications and alterations will occur to others upon a reading and understanding of this specification. It is intending to include all such modifications and alterations insofar as they come within the scope of the appended claims or the equivalence thereof.

Having thus described the invention, I now claim:

1. A catheterization method comprising:
    providing a catheter having a lumen with a flexible distal tip portion;
    providing a first fluid source at a first pressure and connecting the first fluid source to the said lumen through a first fluid supply channel including a check valve operable to block the flow of fluid from the first source whenever the pressure between the said lumen and the check valve exceeds the first pressure;
    providing a second fluid source at a second pressure significantly higher than said first pressure and connecting the second fluid source to the said lumen through a second fluid supply channel including an on-off valve; and,
    at selected times, moving the on-off valve to an on position to provide fluid from the second source to the lumen and move the check valve to block the flow of fluid from the first source.

2. The catheterization method according to claim 1 wherein:
    the step of connecting said first fluid includes communicating the first fluid from the source of the first fluid to the lumen through the first fluid supply channel substantially at 300 mm. of mercury; and,
    the step of connecting the second fluid includes communicating the second fluid from the source of the second fluid to the lumen through the second fluid supply channel substantially at 1,000 PSI.

3. The catheterization method according to claim 1 wherein the step of connecting the first fluid source includes biasing said one-way check valve open by said first fluid at said first pressure in an absence of said second fluid at said second pressure.

4. The catheterization method according to claim 3 further comprising the step of maintaining said first source of fluid at said first pressure while biasing said one-way check valve closed with said second fluid at said second pressure.

5. The catheterization method of claim 1 wherein the first fluid is a saline solution and the second fluid is an opaque dye media and including the step of maintaining the first fluid continuously connected to the check valve while the on-off valve is in an open position.

6. A valve in combination with an elongate hollow catheter and a source of a first pressurized fluid, the valve including:
    a substantially tubular body having a first end and a second end and a fluid passage therethrough and including a continuous circumferential female luer hub threaded for selective engagement with an operatively associated male luer fitting;
    movable means comprising a check ball within the substantially tubular body for opening the fluid passage when in a first position and closing the fluid passage when in a second position;
    biasing means within the substantially tubular body for biasing said check ball toward said second position;
    the check ball and the biasing means being adapted for opening said fluid passage when a first pressure at the first end of the substantially tubular body is greater than a second pressure at the second end of the substantially tubular body; and,
    wherein the first end of the substantially tubular body is connected to said source of first pressurized fluid; and,
    the second end of the substantially tubular body includes an internally threaded cap member having a first end adapted to i) engage a first surface of an operatively associated female luer fitting when the cap member is rotated to a first position and ii) engage a second surface of the operatively associated female luer fitting when the cap member is rotated to a second position; and, further,
    wherein said first end of said cap member includes i) a semi-circular opening for selectively securing the operatively associated female luer fitting; and, ii) a first surface adapted to selectively contact the first surface of the female luer fitting for urging relative motion between the valve and the female luer fitting when the cap member is rotated to beyond said second position.

* * * * *